(12) United States Patent
Mizobe et al.

(10) Patent No.: US 8,917,921 B2
(45) Date of Patent: Dec. 23, 2014

(54) IMAGE PROCESSING APPARATUS AND METHOD WITH CONTROL OF IMAGE TRANSFER PRIORITY

(75) Inventors: Hideaki Mizobe, Tokyo (JP); Kenji Morita, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 130 days.

(21) Appl. No.: 13/207,997

(22) Filed: Aug. 11, 2011

(65) Prior Publication Data
US 2012/0051585 A1    Mar. 1, 2012

(30) Foreign Application Priority Data
Aug. 31, 2010   (JP) ................................ 2010-195070

(51) Int. Cl.
     *G06K 9/00*      (2006.01)
     *G06F 19/00*      (2011.01)
     *G06T 7/00*      (2006.01)

(52) U.S. Cl.
CPC ..... *G06F 19/321* (2013.01); *G06T 2207/30041* (2013.01); *G06T 2207/10101* (2013.01); *G06T 7/0012* (2013.01)
USPC ........................................................ 382/131

(58) Field of Classification Search
USPC ........................ 382/128–134; 128/920–925; 356/39–49; 600/407–414, 424–426; 345/581–618
See application file for complete search history.

(56) References Cited

U.S. PATENT DOCUMENTS

| | | | |
|---|---|---|---|
| 7,566,128 B2 | 7/2009 | Tsukada et al. | 351/205 |
| 7,590,440 B2 | 9/2009 | Lau et al. | 600/413 |
| 7,639,776 B2 | 12/2009 | Gohno et al. | 378/15 |
| 7,857,449 B2 | 12/2010 | Imamura et al. | 351/205 |
| 7,903,854 B2 | 3/2011 | Sakaida et al. | 382/128 |
| 8,254,649 B2 | 8/2012 | Matsue et al. | 382/128 |
| 2003/0174883 A1 | 9/2003 | Krishnan | 382/166 |
| 2005/0259116 A1 | 11/2005 | Araoka | 345/619 |

(Continued)

FOREIGN PATENT DOCUMENTS

| | | |
|---|---|---|
| CN | 1702645 | 11/2005 |
| JP | 04-320579 | 11/1992 |

(Continued)

OTHER PUBLICATIONS

M.K. Garvin et al., "Automated 3-D Intraretinal Layer Segmentation of Macular Spectral-Domain Optical Coherence Tomography Images", *IEEE Transactions on Medical Imaging*, vol. 28, No. 9, pp. 1436-1447 (Sep. 2009).

(Continued)

*Primary Examiner* — Atiba O Fitzpatrick
(74) *Attorney, Agent, or Firm* — Fitzpatrick, Cella, Harper & Scinto

(57) ABSTRACT

An image processing apparatus which uses a tomogram group formed from a plurality of object tomograms or measurement data for generating the plurality of object tomograms, wherein the tomograms parallel to a plane containing first and second directions and aligned in a third direction different from the first and second directions, are provided. The image processing apparatus includes a storage unit which stores the tomogram group. The image processing apparatus specifies a plurality of tomograms from the tomogram group, and sets higher priorities for the specified tomograms or a predetermined number of tomograms adjacent to the specified tomograms than for other tomograms. The image processing apparatus reads out the tomogram group from the storage unit in descending order of the set priorities, and provides it to subsequent processing.

18 Claims, 10 Drawing Sheets

(56) References Cited

U.S. PATENT DOCUMENTS

| | | | |
|---|---|---|---|
| 2007/0127790 A1* | 6/2007 | Lau et al. | 382/128 |
| 2008/0118119 A1 | 5/2008 | Mahesh et al. | 382/128 |
| 2009/0220135 A1 | 9/2009 | Nakamura | 382/128 |

FOREIGN PATENT DOCUMENTS

| | | |
|---|---|---|
| JP | 09-313447 | 12/1997 |
| JP | 2001-309219 | 11/2001 |
| JP | 2005-277669 | 10/2005 |
| JP | 2007-117714 | 5/2007 |
| JP | 2007-325853 | 12/2007 |
| JP | 2008-036262 | 2/2008 |
| JP | 2009-022368 | 2/2009 |
| JP | 2009-515599 | 4/2009 |
| JP | 2009-230755 | 10/2009 |
| JP | 2010-035607 | 2/2010 |
| WO | WO 2005/091219 | 9/2005 |

OTHER PUBLICATIONS

Office Action issued Jan. 11, 2013 in German counterpart application 102011081811.1 (English summary provided above).

GB EESR dated Nov. 30, 2011, issued in connection with counterpart British application GB1113604.1.

Office Action issued on Oct. 24, 2013 in counterpart PRC patent application 201110248469.3, with translation.

British Office Action issued on Jul. 16, 2014, in British (GB) counterpart application 1113604.1.

* cited by examiner

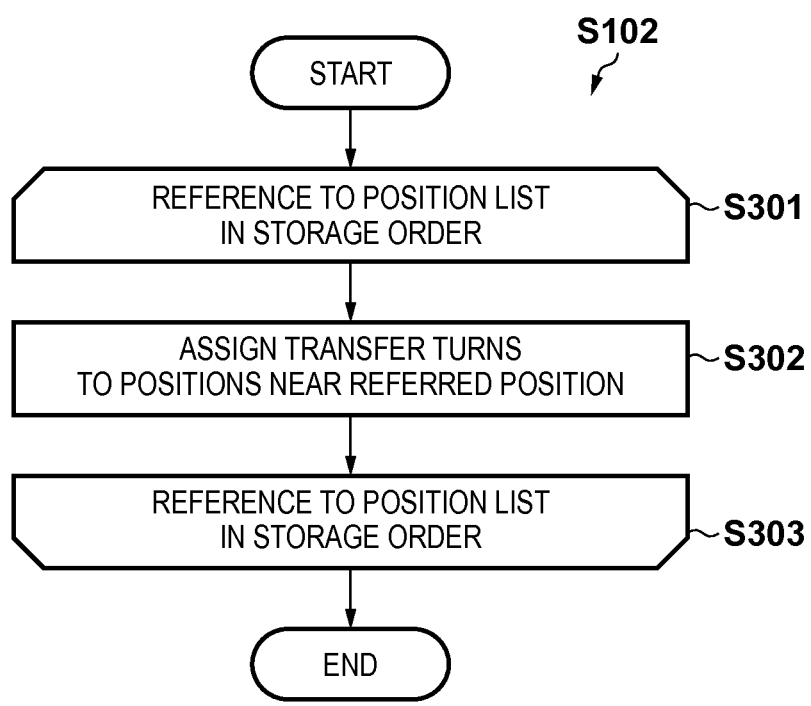

F I G. 7

| SLICE POSITION NUMBER | TOMOGRAM NAME | INPUT PRIORITY |
|---|---|---|
| 1 | Im_1 | 11 |
| 2 | Im_2 | 9 |
| 3 | Im_3 | 7 |
| 4 | Im_4 | 6 |
| 5 | Im_5 | 8 |
| 6 | Im_6 | 10 |
| 7 | Im_7 | |
| 8 | Im_8 | 15 |
| 9 | Im_9 | 13 |
| 10 | Im_10 | 12 |
| 11 | Im_11 | 14 |
| 12 | Im_12 | 16 |
| 13 | Im_13 | |
| 14 | Im_14 | 4 |
| 15 | Im_15 | 2 |
| 16 | Im_16 | 1 |
| 17 | Im_17 | 3 |
| 18 | Im_18 | 5 |
| 19 | Im_19 | |
| 20 | Im_20 | |
| 21 | Im_21 | |
| ⋮ | ⋮ | |
| N | Im_N | |

F I G. 13
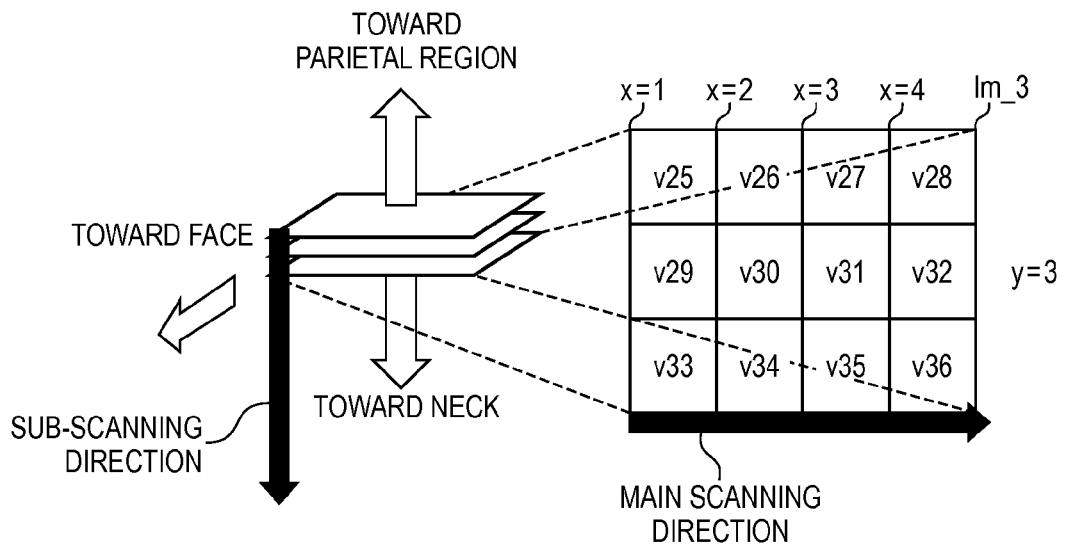
F I G. 14
| INPUT PRIORITY | SLICE POSITION |
|---|---|
| 1 | x=2 |
| 2 | y=3 |
| 3 | x=1 |
| 4 | y=2 |
| 5 | x=3 |
| 6 | y=1 |

IMAGE PROCESSING APPARATUS AND METHOD WITH CONTROL OF IMAGE TRANSFER PRIORITY

BACKGROUND OF THE INVENTION

1. Field of the Invention

The present invention relates to an image processing apparatus using a plurality of tomograms and a control method thereof.

2. Description of the Related Art

There is known a medical tomogram display system including a server which saves a plurality of medical tomogram groups each formed from a plurality of digital images, and an image application terminal which is connected to the server and uses medical tomograms transferred from the server. Recently, improved performance of various modalities provides higher-resolution medical images, and the amount of image data is increasing. This prolongs the image transfer time to the image application terminal from the server which saves image groups. A need exists to shorten the time required until an image becomes usable on the image application terminal.

Conventional methods currently exist to shorten the transfer time between the server and the image application terminal. For example, there is a method of shortening the transfer time by transferring an image group after data compression to decrease the data amount. Japanese Patent Laid-Open No. 2009-230755 (to be referred to as Reference 1) proposes a method of shortening the waiting time by changing the tomogram transfer order to preferentially transfer a tomogram to be used, instead of deciding the tomogram transfer order arbitrarily (e.g., file name order).

However, the data compression ratios are low for noisy images such as those captured by OCT (Optical Coherence Tomography). When the data compression time and data decompression time is considered, the transfer time taken to transfer a noisy image after data compression may become longer than that taken to perform the transfer without data compression. Depending on the image, data compression is sometimes ineffective for transfer processing. The method described in Reference 1 decides the input order in descending order of closeness to the slice position of a given tomogram. A waiting time is generated till the completion of input of a tomogram at a slice position spaced apart from the given tomogram. Even if a tomogram at the region of interest is to be used, it may not be used quickly because input of a required tomogram has not completed.

SUMMARY OF THE INVENTION

The present invention has been made to alleviate the above problems, and provides an image processing apparatus capable of appropriately controlling the tomogram transfer order in order to shorten the waiting time until an image becomes usable, and a control method thereof.

According to one aspect of the present invention, there is provided an image processing apparatus which uses a tomogram group formed from a plurality of object tomograms or measurement data for generating the plurality of object tomograms, wherein the object tomograms are parallel to a plane containing a first direction and a second direction and are aligned in a third direction different from the first direction and the second direction, the apparatus comprising: a storing unit configured to store the tomogram group; a specifying unit configured to specify a plurality of tomograms from the tomogram group; a setting unit configured to set priorities for the tomograms specified by the specifying unit or a predetermined number of tomograms parallelly adjacent to the specified tomograms; and a reading unit configured to read out the tomogram group from the storing unit in descending order of the priorities set by the setting unit.

According to another aspect of the present invention, there is provided a method of controlling an image processing apparatus including a storing unit configured to store a tomogram group formed from a plurality of object tomograms or measurement data for generating the plurality of object tomograms, wherein the tomograms parallel to a plane containing a first direction and a second direction and aligned in a third direction different from the first direction and the second direction, comprising: a specifying step of specifying a plurality of tomograms from the tomogram group; a setting step of setting priorities for the tomograms specified in the specifying step or a predetermined number of tomograms parallelly adjacent to the specified tomograms; and a reading step of reading out the tomogram group from the storing unit in descending order of the priorities set in the setting step.

Further features of the present invention will become apparent from the following description of exemplary embodiments with reference to the attached drawings.

BRIEF DESCRIPTION OF THE DRAWINGS

FIG. 5 is a table exemplifying generation of the position list according to the first embodiment;

FIG. 6 is a flowchart showing an image transfer order decision sequence according to the first embodiment;

FIG. 7 is a table exemplifying transfer order information according to the first embodiment;

FIG. 13 is a view exemplifying the structures of an image group and image according to the second embodiment; and FIG. 14 is a table exemplifying decision of the image transfer order according to the second embodiment.

DESCRIPTION OF THE EMBODIMENTS

Preferred embodiments of the present invention will now be described with reference to the accompanying drawings. In the following description, an image processing apparatus according to the present invention is applied to an ophthalmology image processing apparatus; however the present invention is not limited to the following embodiments.

First Embodiment

Figure 1:
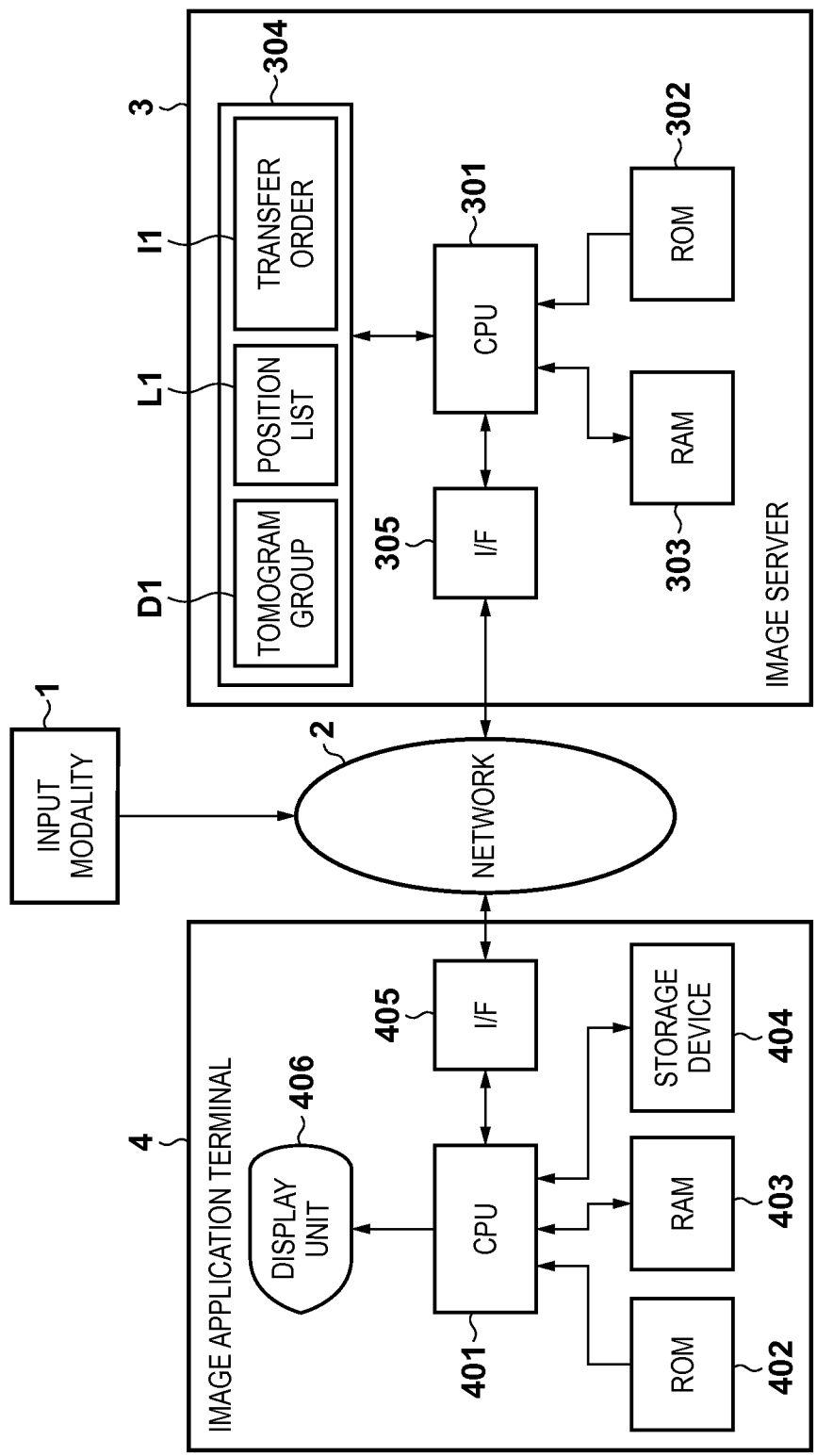
FIG. 1 is a block diagram exemplifying the arrangement of an ophthalmology image processing apparatus according to the first embodiment.

FIG. 1 is a schematic block diagram exemplifying the arrangement of an ophthalmology image processing apparatus according to the first embodiment. As shown in FIG. 1, the ophthalmology image processing apparatus according to the first embodiment is a medical network system in the medical field. An input modality 1 configured to record image data by CT, MRI, OCT, or the like is connected via a network 2 to an image server 3 which saves image groups captured by the input modality 1. The image server 3 is connected via the network 2 to an image application terminal 4 which uses images stored in the image server 3. However, the medical network system is not limited to the system configuration shown in FIG. 1. For example, a network which connects the input modality 1 and image server 3 may be different from one which connects the image server 3 and image application terminal 4. As described above, the ophthalmology image processing apparatus according to the embodiment has an arrangement in which the input modality 1, image server 3, and image application terminal 4 are connected via the network 2. Note that the image server 3 and image application terminal 4 may be formed from a single apparatus.

Figure 2:
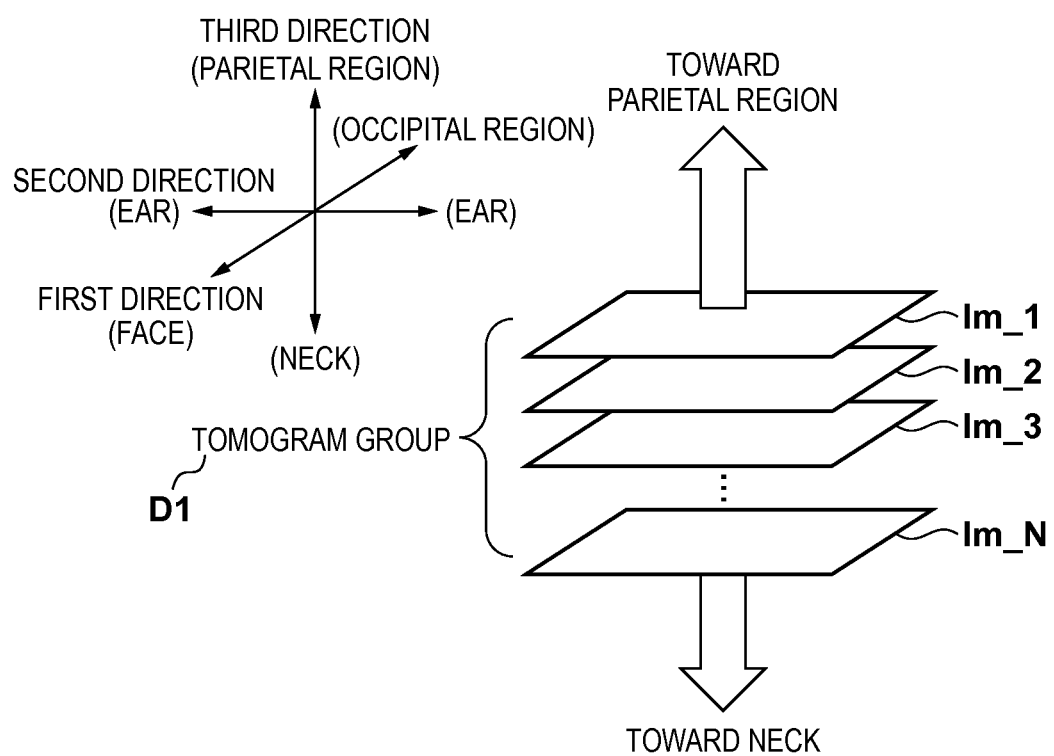
FIG. 2 is a view exemplifying the structure of a tomogram group according to the first embodiment.

In the embodiment, the modality 1 serves as an OCT which images the retina. Object tomograms (retina tomograms in the embodiment) acquired by the input modality 1 are a set of cross sections of a predetermined imaging area, and are formed from a plurality of 2D images, as shown in FIG. 2. Such a 2D image will be called a tomogram. A set of tomograms acquired by the modality 1 will be called a tomogram group D1. The embodiment assumes that the tomogram group D1 includes a plurality of tomograms $Im\_1$, $Im\_2$, $Im\_3$, ..., $Im\_N$ regarding the retina, and the respective tomograms are captured from the parietal region toward the neck in the order named. The tomogram group D1 includes a plurality of object tomograms aligned in the third direction (parietal region-to-neck direction in this example) parallel to a plane containing the first direction (occipital region-to-face direction in this example) and the second direction (direction extending from one side of the face to the other) and different from the first and second directions. In the embodiment, the respective tomograms are assigned position numbers incremented from 1 in order from the parietal region such that the position of the tomogram $Im\_1$ is 1 and that of the tomogram $Im\_{\_2}$ is 2, for descriptive convenience. Note that the tomogram group D1 is a set of object tomograms, but may be measurement data for generating a set of object tomograms.

In the image server 3, a CPU 301 executes various processes in accordance with control programs stored in a ROM 302 or RAM 303. A storage unit 304 stores the tomogram group D1, and a position list L1 and transfer order information I1 to be described later. An interface 305 connects the image server 3 and network 2. In the image application terminal 4, a CPU 401 executes various processes in accordance with control programs stored in a ROM 402 or RAM 403. A tomogram transferred from the image server 3 is stored in a storage device 404 or the RAM 403, and displayed on a display unit 406.

The ophthalmology image processing apparatus in the embodiment has a plurality of functions for specifying, from the tomogram group D1, a plurality of tomograms which are highly likely to be used in the image application terminal 4. The embodiment assumes that the ophthalmology image processing apparatus has five (first to fifth) specifying functions to be described later. Detailed examples of these specifying functions will be explained below.

(1) First Specifying Function: A program running on the image application terminal 4 provides a user interface on the screen of the display unit 406 to designate a tomogram. The user is prompted to designate, via the user interface, the position of a tomogram he or she wants. The user interface can be implemented by displaying, for example, a slider operable by the user, and associating the coordinate of the slider thumb with a tomogram position such that $Im\_1$ corresponding to tomogram position 1 is designated for a slider thumb coordinate of 0. Alternatively, a tomogram may be specified using a GUI as disclosed in Japanese Patent Laid-Open No. 2007-117714.

(2) Second Specifying Function: The tomogram group D1 is analyzed to specify a tomogram containing a lesion. Processing for specifying a lesion-containing tomogram can use a known method as disclosed in Japanese Patent Laid-Open No. 2010-035607.

(3) Third Specifying Function: The tomogram group D1 is analyzed to specify a tomogram containing a specific anatomical region in the object. For example, the third specifying function according to the embodiment specifies a tomogram containing the fovea centralis from a retina tomogram group.

(4) Fourth Specifying Function: The tomogram group D1 is analyzed to specify a tomogram containing a specific anatomical region in the object. For example, the fourth specifying function specifies a tomogram containing the center of the optic papilla from a retina tomogram group. In the third and fourth specifying functions described above, processing for specifying a predetermined anatomical position from the tomogram group D1 can use a known method as disclosed in Japanese Patent Laid-Open No. 09-313447.

(5) Fifth Specifying Function: A function of allowing the user of the system to specify an arbitrary tomogram in advance is provided. To implement this specifying function, the image server 3 suffices to save information capable of specifying an arbitrary tomogram. The "function of specifying an arbitrary tomogram" is used when, for example, the user wants to always preferentially input the first tomogram of a tomogram group. The fifth specifying function can be used when a tomogram independent of a case such as a lesion needs to be input.

The image application terminal 4 in the embodiment transmits, to the image server 3, priority order information indicating the priority order of the first to fifth specifying functions. Assume that the priority order information in the embodiment designates the priority order of the first to fifth specifying functions in the order named. Note that the priority order information may be transmitted in response to a tomogram transfer start request. The priority order of the respective specifying functions may be made settable in the image server 3. Alternatively, the image server 3 may monitor the tomogram use state in the image application terminal 4 and change the priority order of the specifying functions. Upon receiving a transfer start request, the image application terminal 4 may notify the image server 3 of the slider thumb coordinate in the first specifying function.

Figure 3:
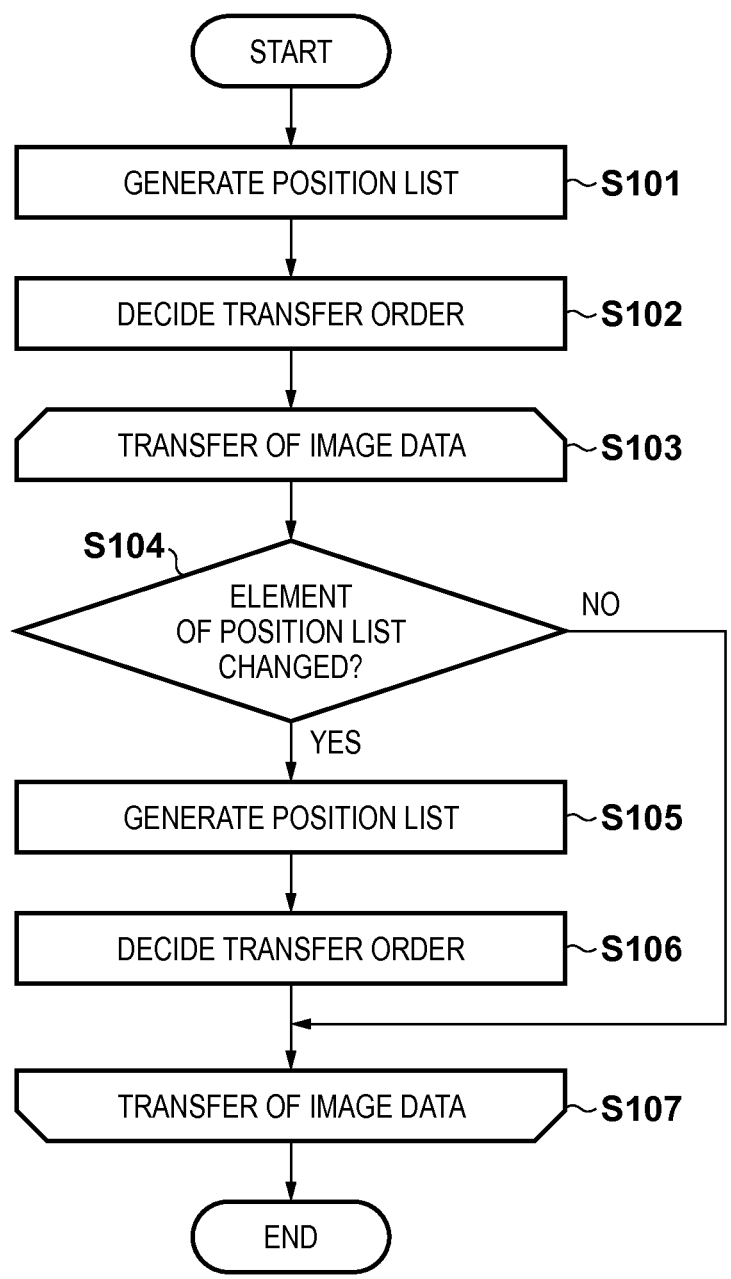
FIG. 3 is a flowchart showing the processing sequence of the ophthalmology image processing apparatus according to the first embodiment.

The operation of the ophthalmology image processing apparatus according to the embodiment will be explained on this premise. FIG. 3 is a flowchart showing the processing sequence of the ophthalmology image processing apparatus in the embodiment. Assume that the storage unit 304 of the image server 3 has already stored the retina tomogram group D1 recorded by the input modality 1 and the priority order information. Note that the processing shown in FIG. 3 is implemented by executing a program stored in the ROM 302 by the CPU 301.

Figure 4:
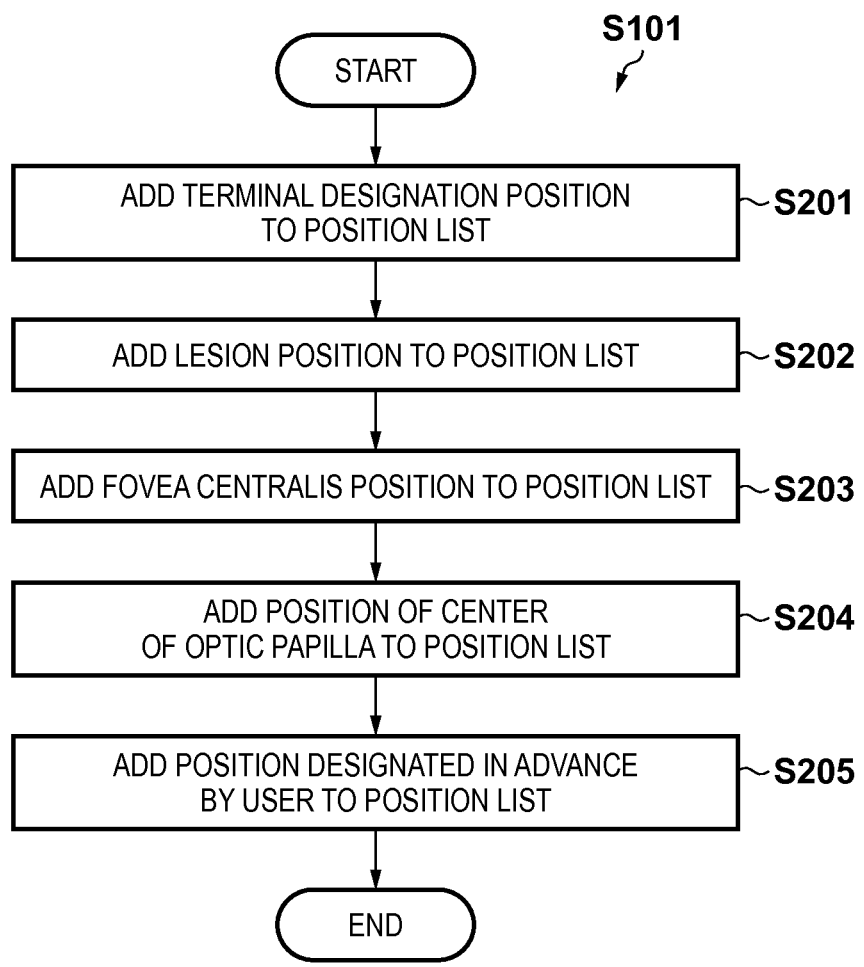
FIG. 4 is a flowchart showing a position list generation sequence according to the first embodiment.

The CPU 301 of the image server 3 receives a tomogram group transfer start instruction from the image application terminal 4 which uses images. In step S101, the position list L1 is generated. In generation of the position list L1, tomograms specified from the tomogram group D1 by the first to fifth specifying functions are registered in the list. FIG. 4 is a flowchart showing a sequence for generating the position list L1 in the ophthalmology image processing apparatus in the first embodiment. The position list L1 stores the positions of tomograms specified by the above-mentioned first to fifth specifying functions in the priority order indicated by the priority order information. More specifically, the position list L1 stores, in the priority order, a position designated via the user interface of the image application terminal 4, that of a tomogram containing a lesion, that of a tomogram containing the fovea centralis, that of a tomogram containing the center of the optic papilla, and that of a tomogram designated in advance by the user of the system.

Note that the position storage order (priority order) in the position list L1 is decided based on the probability of use in the image application terminal 4. In this example, a tomogram at a position designated via the user interface of the image application terminal 4 is most likely to be used in the image application terminal 4. The priority order in the priority order information is changed depending on importance in the image application terminal 4, changing the position storage order in the position list L1 in accordance with the changed priority order. For example, positions specified by the second, third, fourth, and fifth specifying functions, and information about possibilities of use of them may be saved in the image server 3 or image application terminal 4, and the storage order may be changed in accordance with this information. Assume that the possibility of use is set permanently for each specifying function. However, the user may set the possibility of use. In this case, the possibility of use can be set in accordance with a case such as glaucoma or aging macular degeneration. In the above example, the first specifying function specifies a tomogram used for display, and its priority is permanently highest for quick response to the user. That is, the possibility of use of the first specifying function is set to be always highest, and the possibilities of use of the second to fifth functions are changed. However, the present invention is not limited to this, and the possibilities of use of the first to fifth specifying functions may be changed. When a plurality of image application terminals are connected to the image server 3, priority order information may be set for each terminal.

A series of operations in step S101 will be exemplified with reference to FIG. 4. In this example, the position of a tomogram designated via the user interface of the image application terminal 4 is 16, those of tomograms containing a lesion are 4 and 1, that of a tomogram containing the fovea centralis is 10, and there is neither the position of a tomogram containing the center of the optic papilla nor the position of a tomogram designated in advance by the user of the system. Note that the position of a tomogram containing the center of the optic papilla is not obtained when, for example, the center of the optic papilla could not be detected as measurement data.

In step S201, the CPU 301 of the image server 3 stores, in a record of storage number 1 in the position list L1, position 16 serving as a tomogram position corresponding to a position specified by the first specifying function. In step S202, the CPU 301 stores a tomogram position (4 in this example) specified by the second specifying function in a record of storage number 2. In this example, the second specifying function specifies even tomogram position 1, so the CPU 301 stores slice position number 1 in a record of storage number 3. In step S203, the CPU 301 stores slice position number 10 of a tomogram specified by the third specifying function in a record of storage number 4.

In step S204, the CPU 301 stores the position of a tomogram containing the center of the optic papilla. However, there is no information about a position by the fourth specifying function in this example, as described above, so step S204 is skipped. In step S205, the CPU 301 stores a position specified by the fifth specifying function (tomogram position designated in advance by the user of the system). However, there is no information about a position by the fifth specifying function in this example, as described above, and thus step S205 is also skipped. FIG. 5 shows the position list L1 generated as a result of this processing. Note that the storage order can be changed following a change of the priority order in the priority order information by, for example, changing the processing order shown in FIG. 4 in accordance with the changed priority order.

In step S102, the CPU 301 decides the transfer order of the respective tomograms in the tomogram group D1, generating the transfer order information I1. In this case, higher priorities are set for the tomograms registered in the position list L1 or a predetermined number of tomograms adjacent to the registered tomograms than for other tomograms, generating the transfer order information I1. FIG. 6 is a flowchart showing a sequence of deciding the transfer order of tomograms in the first embodiment. In deciding the transfer order, the CPU 301 refers to tomogram positions stored in the position list L1 in the storage order (steps S301 and S303), and tries to assign transfer turns (input priorities) to positions corresponding to an arbitrary number of tomograms near each position (step S302). Transfer turns are assigned to the positions of peripheral tomograms (i.e., a predetermined number of tomograms adjacent to a position specified in the position list L1) because the image application terminal 4 is highly likely to use tomograms near the referred position.

For example, a person mainly operates the slider serving as the first specifying function. It is therefore difficult to accurately move the slider thumb to a desired position by one operation, and fine adjustment for the thumb position is required. However, image display processing can be quickly executed if the image application terminal 4 has already held data of a tomogram at a position to which the thumb position is highly likely to be adjusted finely. For this reason, it is preferable to add even a position near the referred position to the transfer order. However, if no tomogram near the referred position is used, a transfer turn may be assigned to only the referred position. In this transfer turn assignment, transfer turns are decided in descending order of closeness to the referred position based on the 3D positional relationship of the tomogram group D1. Assume that a position referred to in the position list L1 is M in the tomogram group D1 sorted based on the 3D positional relationship. At this time, when assigning transfer turns to five tomograms near the referred position, incremented transfer turns are assigned to positions M, M−1, M+1, M−2, and M+2 in the order named.

In the above processing, no new transfer turn is assigned to a position to which a transfer turn has already been assigned. The position of a non-existent tomogram is ignored. No transfer turn is assigned to the remaining positions to which no transfer turn has been assigned as a result of the operation unless tomograms corresponding to these positions are used in the image application terminal 4. If tomograms at the remaining positions are to be used, their transfer turns are assigned in ascending order of the position and the tomograms are transferred. Alternatively, transfer turns are assigned based on the possibility of use by referring again to the position list L1. The position list L1 is referred to again by, for example, the following procedures: specifically, the number of tomograms to be assigned for each position are doubled (to 10 because it is five in the above example), and transfer turns are calculated again. In step S102, recalculated values (transfer turns) are assigned to positions to which no transfer turn has been assigned.

A series of operations in step S102 will be exemplified in more detail with reference to FIG. 7. Assume that transfer turns are assigned to five tomograms near the position of a tomogram specified in the position list L1. Also, assume that slice position numbers are registered in the position list L1, as shown in FIG. 5. First, a tomogram position at storage number 1 in the position list L1 is 16, and transfer turns are assigned to positions corresponding to five tomograms Im_14 to Im_18 near position 16. More specifically, transfer turns 1, 2, 3, 4, and 5 are assigned to positions 16, 15, 17, 14, and 18 in the order named. Then, a position at storage number 2 in the position list is 4, and transfer turns 6, 7, 8, 9, and 10 are assigned to positions 4, 3, 5, 2, and 6 in the order named. Note that a slice position number for which a transfer turn (input priority) has already been set is skipped. FIG. 7 shows the transfer order information I1 generated as a result of continuing the operation up to storage number 4 in the position list L1.

In steps S103 to S107, the CPU 301 transfers tomogram data in accordance with the transfer order information I1 decided in step S102. Note that data transfer is suspended when an element forming the position list L1, that is, a tomogram position specified by one of the first to fifth specifying functions is changed during transfer. A specified tomogram position is changed in a case in which, for example, the possibility of use (priority) of a specifying function is changed when a group of successive tomograms containing a given region is completed during data transfer. As another case, another algorithm is introduced for the second to fourth specifying functions, and a specified tomogram position is changed. Further, another algorithm (e.g., the sixth specifying function) prepared separately from the first to fifth specifying functions is introduced with higher possibility of use, and a new tomogram is specified. In such a case, steps S105 and S106 (same processes as those in steps S101 and S102) are executed to update the transfer order information I1 and restart data transfer. In the data transfer of steps S103 to S107, transfer completion time is shortened by skipping the transfer of already transferred tomogram data. Transfer of a transferred tomogram is skipped as follows. Specifically, a flag is set to indicate whether transfer has been done for each slice position number in the transfer order information I1 in FIG. 7. When transfer has been done, the flag is set ON. By checking a corresponding flag when transferring a tomogram, it can be determined whether the tomogram has already been transferred. If so, transfer of the tomogram is skipped.

A series of operations in steps S103 to S107 will now be exemplified. Referring to FIG. 7 showing the transfer order decided in step S102, data are transferred in order of Im_16, Im_15, Im_17, Im_14, Im_18, ..., Im_11, Im_8, and Im_12 in accordance with turns indicated by input priorities. In the operation example of step S101 of the embodiment, a slice position to be displayed on the image application terminal 4 is 16. Upon completion of data transfer of the tomogram Im_16 corresponding to position 16, the image application terminal 4 can start display processing on the screen for the tomogram designated with the slider thumb (first specifying function).

Note that the image server may execute the processes in steps S101 and S102 in advance after acquiring a tomogram group regardless of an image transfer start instruction or the like from the image application terminal 4. Priorities are assigned to five tomograms for each specifying function in the embodiment, but the number of tomograms is not limited to this. The number of tomograms to which priorities are set may be changed for each specifying function. Further, the number of tomograms to which priorities are set may be made settable for each specifying function.

The first embodiment can shorten the time until an image can first be used after the start of a tomogram group transfer. In particular, when displaying a given image from an image group on the image application terminal 4, the embodiment can transfer a necessary image first. This can greatly shorten the time until an image can first be used, compared to a conventional method of transferring images in image file name order, beginning with a first image.

Second Embodiment

Figure 8:
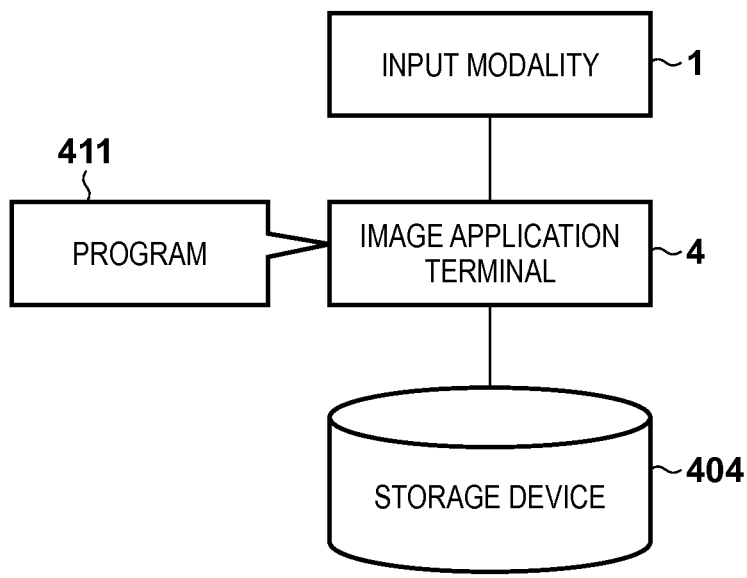
FIG. 8 is a block diagram showing the functional arrangement of an ophthalmology image processing apparatus according to the second embodiment.

FIG. 8 is a schematic block diagram showing the arrangement of an ophthalmology image processing apparatus according to the second embodiment. As shown in FIG. 8, the ophthalmology image processing apparatus according to the second embodiment is a medical system in the medical field. A storage device 404 incorporated in an image application terminal 4 saves image data captured by an input modality 1 configured to record image data by CT, MRI, OCT, or the like. A program 411 for image display runs on the image application terminal 4. The second embodiment will be explained using an arrangement as shown in FIG. 8 (arrangement in which an image server 3 and the image application terminal 4 are integrated), but is also applicable to an arrangement in which the application terminal and server are connected via a network, like the first embodiment. In this case, not the storage device 404 but the image server 3 provides a tomogram via a network 2.

Figure 9:
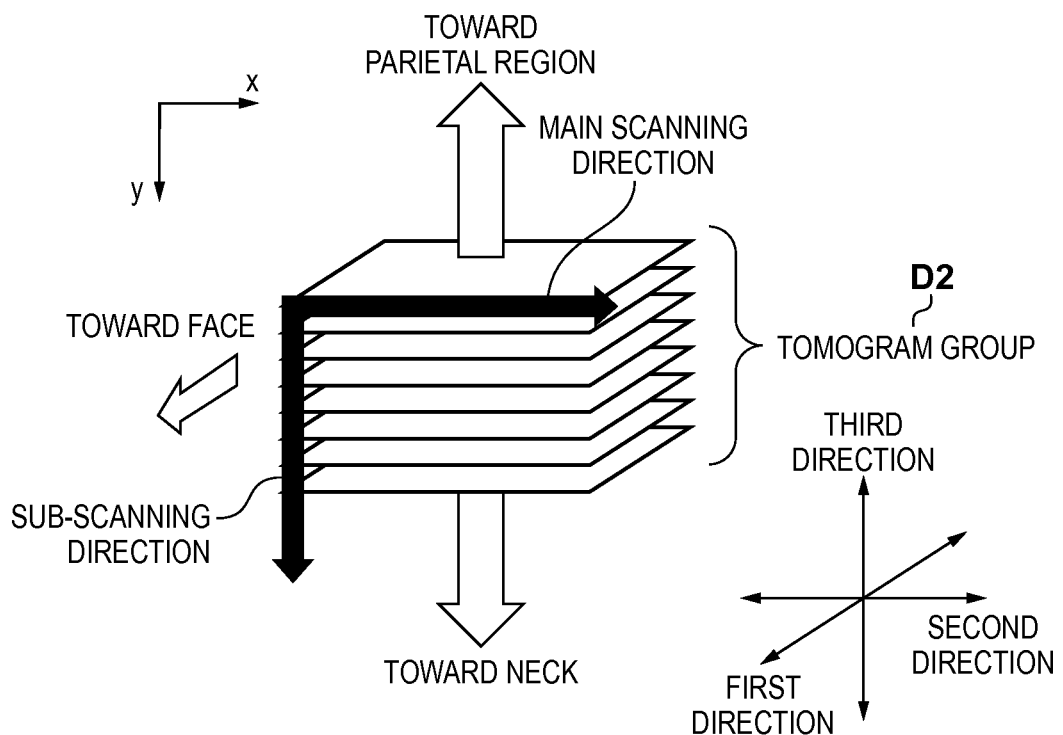
FIG. 9 is a view showing the main scanning direction and sub-scanning direction according to the second embodiment.

Also in the second embodiment, similar to the first embodiment, the input modality 1 serves as an OCT which images the retina. Images captured by the input modality 1 are a set of cross sections of a predetermined imaging area, and the set is a tomogram group D2 formed from a plurality of tomograms (2D images), as shown in FIG. 9. The tomogram group D2 includes a plurality of tomograms Im_1, Im_2, Im_3, . . . , Im_N, and the respective tomograms are captured from the parietal region toward the neck in the order named.

FIG. 9 shows the main scanning direction and sub-scanning direction in the second embodiment. When a tomogram group obtained by imaging the retina is arranged with the parietal region being oriented up, the neck being oriented down, and the face being oriented front, the main scanning direction is the lateral direction (second direction in the first embodiment) and the sub-scanning direction is the longitudinal direction (third direction in the first embodiment). In the second embodiment, when the upper left corner on the near side is defined as the origin of the main scanning direction and sub-scanning direction shown in FIG. 9, x is a coordinate value in the main scanning direction and y is a coordinate value in the sub-scanning direction.

Figure 11:
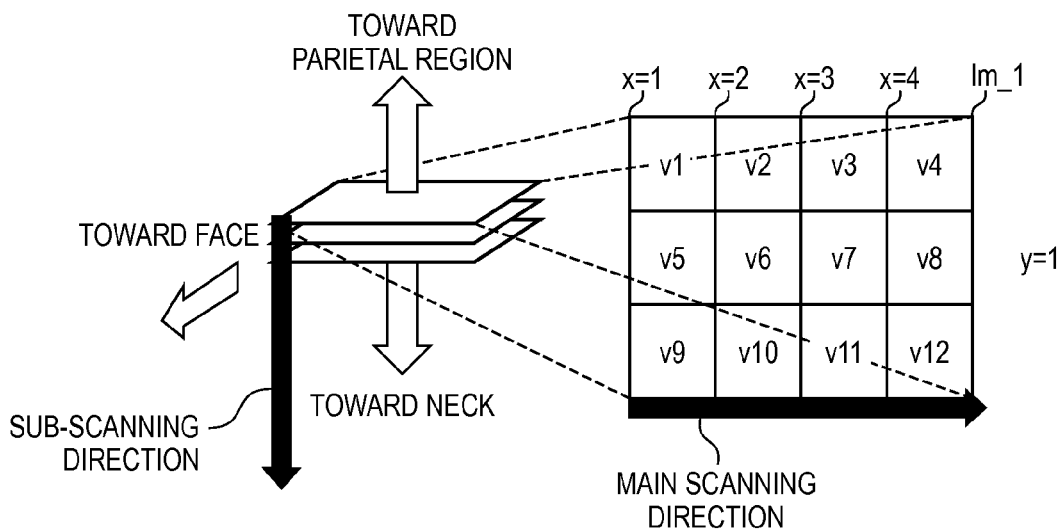
FIG. 11 is a view exemplifying the structures of an image group and image according to the second embodiment.
Figure 12:
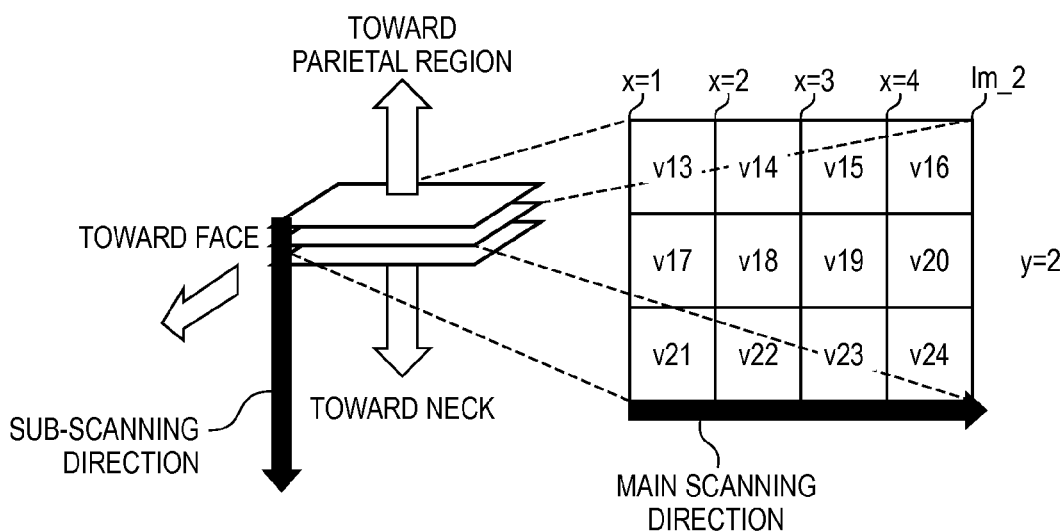
FIG. 12 is a view exemplifying the structures of an image group and image according to the second embodiment.

For example, each of the tomogram groups in FIGS. 11 to 13 includes three tomograms Im_1, Im_2, and Im_3, and each tomogram is a 2D image of 4×3 pixels. FIG. 11 is a view showing in detail the position of the tomogram Im_1 at y=1 in the tomogram group D2 and pixel data forming the tomogram. Similarly, FIG. 12 is a view showing in detail the tomogram Im_2 at y=2, and FIG. 13 is a view showing in detail the tomogram Im_3 at y=3. For example, when the program 411 requires a tomogram at y=1, the values v1, v2, v3, . . . , v12 of pixels forming Im_1 are transferred from the storage device 404 and reconstructed into a tomogram by the program 411. When the program 411 requires a tomogram at x=1, the values of pixels forming the x=1 column in each of Im_1, Im_2, and Im_3 are transferred from the storage device 404. More specifically, values v1, v5, v9, v13, v17, v21, v25, v29, and v33 and transferred from the storage device 404 and reconstructed into a tomogram by the program 411.

In the second embodiment, a tomogram in the main scanning direction means a tomogram which forms a tomogram group, such as Im_1, and its position is indicated by the y-coordinate. A tomogram in the sub-scanning direction means a tomogram which is perpendicular to the main scanning direction with its plane facing toward the ear, and its position is indicated by the x-coordinate.

The ophthalmology image processing apparatus in the second embodiment has a plurality of functions (first to third specifying functions in this example) of specifying, from the tomogram group D2, the position of a tomogram which is highly likely to be used in the program 411. As described above, in the second embodiment, a plurality of specifying functions specify a tomogram parallel to an arbitrary plane from 3D tomogram data which can be formed from the tomogram group D2. In the second embodiment, a position list L2 specifies a tomogram parallel to a plane containing the first and second directions and a tomogram parallel to a plane containing the first and third directions are specified in the 3D space. The first to third specifying functions will be explained below.

First Specifying Function: A coordinate value in the main scanning direction is specified via a user interface which is provided on the screen of a display unit 406 by the program 411 running on the image application terminal 4. For example, the first slider is provided to specify a coordinate X1 in the main scanning direction. To implement the first specifying function, it suffices to associate a thumb coordinate with a coordinate value x in the main scanning direction such that x=1 for a slider thumb coordinate of 0.

Second Specifying Function: A coordinate value in the sub-scanning direction is specified via a user interface which is provided on the screen of the display unit 406 by the program 411 running on the image application terminal 4. For example, the second slider is provided to specify a coordinate Y1 in the sub-scanning direction. To implement the second specifying function, it suffices to associate a thumb coordinate with a coordinate value y in the sub-scanning direction such that y=1 for a slider thumb coordinate of 0. In the second embodiment, the program 411 displays, on the screen, two images, that is, a tomogram at x=X1 specified by the first specifying function and a tomogram at y=Y1 specified by the second specifying function.

Third Specifying Function: The tomogram group D2 is analyzed to specify a tomogram containing a specific anatomical region in the object. For example, by using the method disclosed in, Japanese Patent Laid-Open No. 09-313447, tomograms containing the center of the optic papilla in the sub-scanning direction and main scanning direction are specified to output the coordinate X2 of the tomogram in the sub-scanning direction and the coordinate Y2 of the tomogram in the main scanning direction.

An operation in the second embodiment on the above premise will be explained with reference to the flowchart of FIG. 3. Assume that the storage device 404 serving as the storage unit of the image application terminal 4 has already saved the tomogram group D2 of the retina recorded by the input modality 1, and the coordinates X2 and Y2 obtained as a result of analyzing the tomogram group D2 by the third specifying function.

Figure 10:
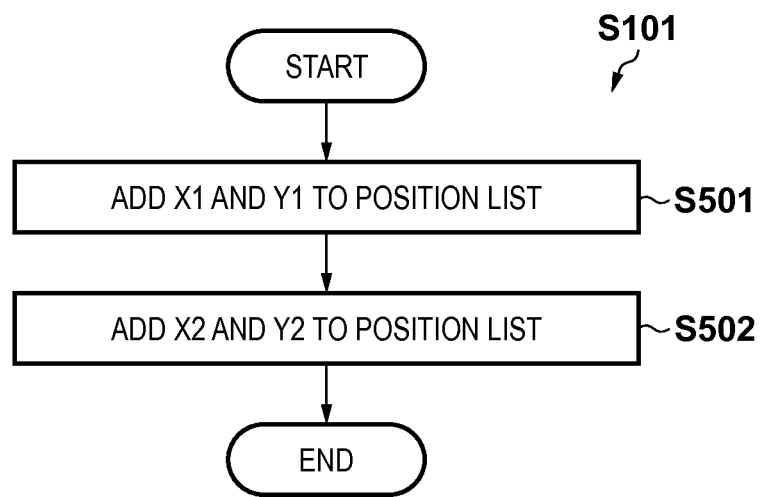
FIGS. 10A and 10B are a flowchart and table, respectively, exemplifying a position list generation sequence and position list according to the second embodiment.

When the program 411 which is to use an image issues an image group transfer start instruction, a CPU 401 of the image application terminal 4 generates the position list L2 in step S101. FIG. 10A is a flowchart showing a sequence of generating the position list L2 in the ophthalmology image processing apparatus in the second embodiment. The position list L2 in the second embodiment can store a coordinate x in the main scanning direction and a coordinate y in the sub-scanning direction for one record. First, the coordinate X1 specified by the first specifying function is stored in x of a record of storage number 1, and the coordinate Y1 specified by the second specifying function is stored in y (S501). Then, the coordinate X2 specified by the third specifying function is stored in x of a record of storage number 2, and the coordinate Y2 specified by the third specifying function is stored in y (S502). This coordinate storage order in the position list L2 is decided based on the possibility of use by the program 411. In this case, the program 411 is highly likely to use tomograms in the sub-scanning direction and main scanning direction that are displayed by the program 411. Similar to the first embodiment, the coordinate storage order in the position list L2 is changeable and is changed based on, for example, importance in the program 411.

An operation of generating the position list L2 in step S101 will be exemplified. Assume that tomograms specified via user interfaces provided by the program 411, that is, the first and second specifying functions are a tomogram at x=2 and a tomogram at y=3. Also in this example, the coordinates of the center of the optic papilla that are specified by the third specifying function are x=1 and y=1. First, in step S501, X1 and Y1, that is, x=2 and y=3, are stored in a record of storage number 1 in the position list. Then, in step S502, X2 and Y2, that is, x=1 and y=1, are stored in a record of storage number 2. FIG. 10B exemplifies the data structure of the position list L2 generated as a result of this processing.

In step S102, the transfer order is decided. In setting of transfer order information, higher priorities are set for tomograms specified in the position list L2 or a predetermined number of tomograms parallelly adjacent to the specified tomograms than for other tomograms. In deciding the transfer order, the coordinates of tomograms stored in the position list L2 are referred to in the storage order, and transfer turns are assigned to the coordinates of an arbitrary number of tomograms, generating transfer order information 12. Transfer turns are assigned to the coordinates of peripheral tomograms because the program 411 is highly likely to use tomograms near the referred coordinate. For example, a person mainly operates the first slider serving as the first specifying function. It is difficult to accurately move the thumb to an arbitrary position by one operation, and the thumb position is finely adjusted. However, image display processing can be quickly executed if a memory, which can be referred to by the program 411, has already held data of a tomogram at a coordinate to which the thumb position is highly likely to be finely adjusted. Thus, even a coordinate near the referred coordinate should be added to the transfer order. However, if no tomogram near the referred coordinate is used, a transfer turn is assigned to only the referred coordinate.

In this transfer turn assignment, transfer turns are decided in descending order of closeness to the referred coordinate based on the 3D positional relationship of the tomogram group D2. A case in which the position list L2 stores a record of x=X and y=Y for the tomogram group D2 sorted based on the 3D positional relationship and transfer turns are assigned to three tomograms near the coordinate will now be explained. In this case, incremented transfer turns are sequentially assigned to tomograms at coordinates x=X, y=Y, x=X−1, y=Y−1, x=X+1, and y=Y+1. Although transfer turns are alternately assigned to coordinates in the main scanning direction and those in the sub-scanning direction, the assignment order may be changed in accordance with the use in the program 411. For example, when the program 411 preferentially uses tomograms in the sub-scanning direction, transfer turns may be sequentially assigned to tomograms at x=X, x=X−1, x=X+1, y=Y, y=Y−1, and y=Y+1.

In the above processing, no new transfer turn is assigned to a coordinate to which a transfer turn has already been assigned. A non-existent coordinate is ignored. No transfer turn is assigned to a coordinate to which no transfer turn has been assigned as a result of the operation unless the program 411 uses a tomogram corresponding to the coordinate. If the tomogram at this coordinate is to be used, a transfer turn is assigned. For example, transfer turns are assigned in ascending order of coordinates in the sub-scanning direction. Alternatively, transfer turns are assigned based on the possibility of use by referring again to the position list L2.

A series of operations in step S102 will be exemplified. A case in which the tomogram group includes three tomograms Im_1, Im_2, and Im_3, and each tomogram is a 2D image of 4×3 pixels will be explained. FIG. 11 is a view showing in detail the position of the tomogram Im_1 at y=1 in the tomogram group and pixel data forming the tomogram. FIG. 12 is a view showing in detail the tomogram Im_2 at y=2, and FIG. 13 is a view showing in detail the tomogram Im_3 at y=3. Assume that transfer turns are assigned to coordinates corresponding to three tomograms near one coordinate. Further, the position list shown in FIG. 10B is used.

First, assignment is attempted of transfer turns to three tomograms near the coordinates x=2 and y=3 at storage number 1 in the position list. More specifically, transfer turns 1, 2, 3, 4, and 5 are assigned to tomograms at x=2, y=3, x=1, y=2, and x=3. Note that an image at y=4 corresponding to Y+1 does not exist and is ignored. Since coordinates at storage number 2 in the position list are x=1 and y=1, transfer turn 6 is assigned to a tomogram at y=1 to which no transfer turn has been assigned yet. FIG. 14 exemplifies transfer order information generated as a result of continuing the above operation.

Finally in steps S103 to S107, tomogram data are transferred in the transfer order decided in step S102. When reading out a tomogram parallel to a plane containing the first and third directions from the storage device 404 in step S103, a partial image forming a tomogram is read out from each tomogram of the tomogram group D2 (details of which will be described later). If an element forming the position list L2, that is, one of tomogram coordinates specified by the first to third specifying functions, is changed during transfer, data transfer is suspended, and the same processes as steps S101 and S102 are performed (steps S105 and S106). Upon completion of changing the position list, data transfer restarts. After the restart of image data transfer, transfer of transferred tomogram data is skipped, shortening the time till the completion of transfer.

In the second embodiment, two tomograms in the main scanning direction and sub-scanning direction are perpendicular to each other, and pixels are shared at crossing positions. If a tomogram in the sub-scanning direction is transferred after transferring a tomogram in the main scanning direction, shared pixel data are redundantly transferred again. The transfer time is shortened by prohibiting re-transfer of the shared pixel data.

A series of operations in step S103 will be exemplified. Referring to FIG. 14 showing the transfer order decided in step S102, data are transferred in order of tomograms at x=2, y=3, x=1, y=2, x=3, and y=1. For example, the tomogram group includes three tomograms Im_1, Im_2, and Im_3, and each tomogram is a 2D image of 4×3 pixels. FIG. 11 is a view showing in detail the position of the tomogram Im_1 at y=1 in the tomogram group and pixel data forming the tomogram. Similarly, FIG. 12 is a view showing in detail the tomogram Im_2 at y=2, and FIG. 13 is a view showing in detail the tomogram Im_3 at y=3. In this example, no redundant pixel data is transferred again.

Pixel data necessary for a tomogram at x=2 specified with transfer turn 1 are v2, v6, v10, v14, v18, v22, v26, v30, and v34, which are transferred. Pixel data necessary for a tomogram at y=3 specified with transfer turn 2 are v25, v27, v28, v29, v31, v32, v33, v35, and v36, which are transferred. The pixel data v26, v30, and v34 contained in the tomogram at y=3 have already been transferred, and are not transferred here. Pixel data necessary for a tomogram at x=1 specified with transfer turn 3 are v1, v5, v9, v13, v17, and v21, which are transferred. The pixel data v25, v29, and v33 contained in the tomogram at x=1 have already been transferred, and are not transferred here.

In the same manner, pixel data necessary for a tomogram at y=2 specified with transfer turn 4 are v15, v16, v19, v20, v23, and v24, which are transferred. Pixel data necessary for a tomogram at x=3 specified with transfer turn 5 are v3, v7, and v11, which are transferred. Pixel data necessary for a tomogram at y=1 specified with transfer turn 6 are v4, v8, and v12, which are transferred. In the operation example of step S101 according to the second embodiment, the program 411 displays tomograms at the coordinates x=2 and y=3. Thus, upon completion of transferring pixel data v2, v6, v10, v14, v18, v22, v26, v30, v34, v25, v27, v28, v29, v31, v32, v33, v35, and v36, the program 411 can start display processing for two tomograms on the screen of the display unit 406.

Other Embodiments

In the above embodiments, the present invention is implemented by adopting OCT for the input modality. However, the embodiments of the present invention can obtain the same effects even for other input modalities such as CT and MRI.

The embodiments of the present invention are not limited to transfer of an image, and a measurement result corresponding to an image may be transferred. Examples are a vector image capable of reproducing an image shape, and coordinate information of a graph obtained by measuring the thickness of the retina.

The above embodiments have exemplified display of a tomogram as an image application method in the image application terminal 4. However, the present invention is not limited to the display, and is applicable to all image processes in the image application terminal 4, such as tomogram measurement processing. Quickly acquiring a whole necessary tomogram group can shorten the waiting time till the start of processing.

In the first embodiment, the transfer order is decided after transfer start processing. However, the processes in steps S101 and S102 can be skipped by having the image server 3 perform measurement processing in advance, which saves the tomogram group D1, and deciding the transfer order.

The present invention can appropriately control the tomogram transfer order, shortening the waiting time until an image becomes usable in the image processing apparatus.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, non-transitory computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-195070, filed Aug. 31, 2010, which is hereby incorporated by reference herein in its entirety.

What is claimed is:

1. An image processing apparatus which uses a tomogram group formed from a plurality of object tomograms or measurement data for generating the plurality of object tomograms, wherein the object tomograms are parallel to a plane containing a first direction and a second direction and are aligned in a third direction different from the first direction and the second direction, said apparatus comprising:
a storing unit configured to store the tomogram group;
a specifying unit configured to specify a plurality of tomograms from the tomogram group;
a setting unit configured to set priorities for at least one of
(a) the tomograms specified by said specifying unit and
(b) a predetermined number of tomograms parallelly adjacent to the specified tomograms; and
a reading unit configured to read out at least one tomogram included in the tomogram group from said storing unit in descending order of the priorities set by said setting unit,
wherein said specifying unit is configured to specify, based on analysis of tomograms from the tomogram group to identify tomogram(s) in the group that contain(s) a predetermined a lesion, as one of the plurality of tomograms, a tomogram including a lesion, and said setting unit is configured to assign a high priority to that tomogram.

2. An apparatus according to claim 1, wherein said specifying unit is configured to specify the plurality of tomograms using different methods.

3. An apparatus according to claim 1, wherein said specifying unit provides a user interface for designating an arbitrary tomogram, and specifies, as one of the plurality of tomograms, a tomogram designated by a user via the user interface.

4. An apparatus according to claim 1, wherein said setting unit is configured to set higher priorities for the predetermined number of tomograms in descending order of closeness to the tomograms specified by said specifying unit.

5. An apparatus according to claim 1, wherein
said specifying unit is configured to specify a tomogram parallel to a plane containing the first direction and the second direction and a tomogram parallel to a plane containing the first direction and the third direction in a three-dimensional space defined by the tomogram group, and
when reading out the tomogram parallel to the plane containing the first direction and the third direction, said reading unit is configured to read out, from each tomogram of the tomogram group, a partial image forming the tomogram.

6. An apparatus according to claim 1, wherein
when the tomogram specified by said specifying unit is changed, said setting unit is configured to set again a priority order in accordance with tomograms newly specified by said specifying unit, and
said reading unit is configured to read out the tomogram group from said storing unit in descending order of the priorities set by said setting unit, except for a tomogram which has already been loaded.

7. An apparatus according to claim 1, wherein
the image processing apparatus includes a terminal apparatus which uses the tomogram group, and an image server including said storing unit, said image server and said terminal apparatus being connected via a network, and
said reading unit is configured to transmit the tomogram group from said image server to said terminal apparatus via the network.

8. A method of controlling an image processing apparatus including a storing unit configured to store a tomogram group formed from a plurality of object tomograms or measurement data for generating the plurality of object tomograms, wherein the tomograms parallel to a plane containing a first direction and a second direction and aligned in a third direction different from the first direction and the second direction, comprising:
a specifying step of specifying a plurality of tomograms from the tomogram group;
a setting step of setting priorities for at least one of (a) the tomograms specified in the specifying step and (b) a predetermined number of tomograms parallelly adjacent to the specified tomograms; and
a reading step of reading out at least one tomogram included in the tomogram group from the storing unit in descending order of the priorities set in the setting step,
wherein, in said specifying step, based on analysis of tomograms from the tomogram group to identify tomogram(s) in the group that contain(s) a lesion, there is specified as one of the plurality of tomograms, a tomogram including a lesion, and in said setting step, a high priority is assigned to that tomogram.

9. A computer-readable non-transitory storage medium storing a program that, when executed by an image processing apparatus, causes the image processing apparatus to perform a method according to claim 8.

10. An image processing apparatus which uses a tomogram group formed from a plurality of object tomograms or measurement data for generating the plurality of object tomograms, wherein the object tomograms parallel to a plane containing a first direction and a second direction and are aligned in a third direction different from the first direction and the second direction, said apparatus comprising:
a storing unit configured to store the tomogram group;
a specifying unit configured to specify a tomogram from the tomogram group, which includes a lesion, the specifying being done based on analysis of tomograms in the tomogram group to identify tomogram(s) containing the lesion;
a setting unit configured to set priorities for at least one of
(a) the tomograms specified by said specifying unit and
(b) a predetermined number of tomograms parallelly adjacent to the specified tomograms; and a reading unit configured to read out at least one tomogram included in the tomogram group from said storing unit in descending order of the priorities set by said setting unit.

11. A method of controlling an image processing apparatus including a storing unit configured to store a tomogram group formed from a plurality of object tomograms or measurement data for generating the plurality of object tomograms, wherein the tomograms parallel to a plane containing a first direction and a second direction and aligned in a third direction different from the first direction and the second direction, comprising:
- a specifying step of specifying a tomogram from the tomogram group, which includes a lesion, the specifying being done based on analysis of tomograms in the tomogram group to identify tomogram(s) containing the lesion;
- a setting step of setting priorities for at least one of (a) the tomograms specified in said specifying step and (b) a predetermined number of tomograms parallelly adjacent to the specified tomograms; and
- a reading step of reading out at least one tomogram included in the tomogram group from the storing unit in descending order of the priorities set in specifying setting step.

12. An image processing apparatus which uses a tomogram group formed from a plurality of object tomograms or measurement data for generating the plurality of object tomograms, wherein the object tomograms parallel to a plane containing a first direction and a second direction and are aligned in a third direction different from the first direction and the second direction, said apparatus comprising:
- a storing unit configured to store the tomogram group;
- a specifying unit configured to specify a tomogram from the tomogram group, which includes an optic papilla or fovea centralis, the specifying being done based on analysis of tomograms in the tomogram group to identify a tomogram containing the optic papilla or fovea centralis;
- a setting unit configured to set priorities for at least one of (a) the tomograms specified by said specifying unit and (b) a predetermined number of tomograms parallelly adjacent to the specified tomograms; and
- a reading unit configured to read out at least one tomogram included in the tomogram ground from said storing unit in descending order of the priorities set by said setting unit.

13. A method of controlling an image processing apparatus including a storing unit configured to store a tomogram group formed from a plurality of object tomograms or measurement data for generating the plurality of object tomograms, wherein the tomograms parallel to a plane containing a first direction and a second direction and aligned in a third direction different from the first direction and the second direction, comprising:
- a specifying step of specifying a tomogram from the tomogram group, which includes an optic papilla or fovea centralis, the specifying being done based on analysis of tomograms in the tomogram group to identify a tomogram containing the optic papilla or fovea centralis;
- a setting step of setting priorities for at least one of (a) the tomograms specified in said specifying step and (b) a predetermined number of tomograms parallelly adjacent to the specified tomograms; and
- a reading step of reading out at least one tomogram included in the tomogram group from the storing unit in descending order of the priorities set in said setting step.

14. A method according to claim 8, wherein the setting step includes a step of setting higher priorities for the predetermined number of tomograms in descending order of closeness to the tomograms specified in the specifying step.

15. An apparatus according to claim 1, wherein said setting unit is configured to set higher priorities for the predetermined number of tomograms in descending order of closeness to the tomograms specified by said specifying unit.

16. A method according to claim 11, wherein the setting step includes a step of setting higher priorities for the predetermined number of tomograms in descending order of closeness to the tomograms specified in the specifying step.

17. An apparatus according to claim 12, wherein said setting unit is configured to set higher priorities for the predetermined number of tomograms in descending order of closeness to the tomograms specified by said specifying unit.

18. A method according to claim 13, wherein the setting step includes a step of setting higher priorities for the predetermined number of tomograms in descending order of closeness to the tomograms specified in the specifying step.

* * * * *